(12) United States Patent
Luo et al.

(10) Patent No.: US 7,811,593 B2
(45) Date of Patent: Oct. 12, 2010

(54) PHARMACEUTICAL COMPOSITION WITH COMBINED ACTIVE AGENTS AND METHODS FOR USING THE SAME

(76) Inventors: Jian Luo, 240 Klamath St., Brisbane, CA (US) 94005; Hui Chang Wu, 240 Klamath St., Brisbane, CA (US) 94005

( * ) Notice: Subject to any disclaimer, the term of this patent is extended or adjusted under 35 U.S.C. 154(b) by 817 days.

(21) Appl. No.: 10/507,382

(22) PCT Filed: Mar. 10, 2003

(86) PCT No.: PCT/US03/07388

§ 371 (c)(1),
(2), (4) Date: Sep. 9, 2004

(87) PCT Pub. No.: WO03/082283

PCT Pub. Date: Oct. 9, 2003

(65) Prior Publication Data

US 2005/0165109 A1    Jul. 28, 2005

(51) Int. Cl.
*A61K 9/00* (2006.01)
(52) U.S. Cl. .................................................. 424/400
(58) Field of Classification Search ........................ None
See application file for complete search history.

(56) References Cited

U.S. PATENT DOCUMENTS 5,922,769 A * 7/1999 Barelli et al. ............... 514/616

FOREIGN PATENT DOCUMENTS

FR      2796940 A1 *  2/2001
WO   WO 9805331 A2 *  2/1998

OTHER PUBLICATIONS

Ko et al, Comparison of the Effects of Gemfibrozil (600 MG Twice Daily and 900 MG Once Daily) on Lipid and Glucose Levels in Chinese Patients with Non-Insulin-Dependent Diabetes Mellitus, Current Therapuetic Research, 56 (10), 1995, 1033-1040.*
Marrapodi et al, Peroxisome Proliferator-Activated Receptor alpha (PPARalpha) and Agonist Inhibit Cholesterol 7alpha-Hydroxylase Gene (CYP7A1) Transcription, Journal of Lipid Research, 41, 2000, 514-520.*
Weintraub et al, Effects of fibric acid derivatives and metformin on postprandial lipemia, Atherosclerosis, 1998, 141 Suppl 1, S71-S75.*
FR 2796940A1 English Abstract.*
http://www.webmd.com/diet/what-is-obesity (accessed Jan. 3, 2009) p. 1.*
http://www.webmd.com/diet/what-is-obesity (accessed Jan. 3, 2009) p. 2.*

* cited by examiner

*Primary Examiner*—Michael G Hartley
*Assistant Examiner*—Paul Dickinson

(57) ABSTRACT

The current invention involves a pharmaceutical composition containing a combination of two active agents. The invention also involves the use of the combination composition to the preparation of a drug combination intended to treat, control and prevent type 2 diabetes and other diseases and conditions that glucose abnormality, including abnormalities in glucose levels and glucose metabolism, is a component.

3 Claims, No Drawings

PHARMACEUTICAL COMPOSITION WITH COMBINED ACTIVE AGENTS AND METHODS FOR USING THE SAME

FIELD OF INVENTION

The current invention involves a pharmaceutical composition containing a combination of two active agents. The invention also involves the use of the combination composition to the preparation of a drug combination intended to treat, control and prevent type 2 diabetes or other diseases and conditions that glucose abnormality, including abnormalities in glucose levels and glucose metabolism, is a component.

BACKGROUND

Diabetes mellitus is characterized by abnormal plasma glucose level. There are more than 16 millions patients with diabetes mellitus in the United States. Among them, 90-95% are type 2 diabetes, which is characterized by insulin resistance and relative insulin deficiency. It is a serious health problem. Health care costs related to diabetes are over $100 billions/year in the United States.

Current treatment for type 2 diabetes includes oral glucose-lowering agents and insulin. There are four major classes of oral glucose lowering agents, including biguanides (e.g., metformin), sulfonylureas (e.g., glyburide), thiazolidinediones and alpha-glucosidase inhibitors. As the recent understanding of the importance of normalizing plasma glucose to prevent the development of diabetic complications, the magnitude of the glucose-lowering effect with monotherapy is often not satisfactory. There has been a trend to combine agents from different classes to achieve better glucose control. One example is Glucovance (Bristol-Myers Squibb), which is a combination of metformin and glyburide, two commonly use oral glucose-lowering agents.

Type 2 diabetes is a complicated disease. In addition to elevated plasma glucose concentration, other abnormalities also involve in the development of complications. Most of patients with type 2 diabetes are dyslipidemic, as characterized by high triglycerides, small dense LDL (Low Density Lipoprotein), LDL-cholesterol and low HDL (High Density Lipoprotein)-cholesterol. These abnormalities obviously contribute to the development of cardiovascular complications. None of the current oral glucose-lowering agents satisfactorily improve dyslipidemia, nor do the combination of these agents. There is a need for better control of hyperglycemia and improving dyslipidemia at the same time.

Metformin is a member of biguanides. It has been widely used in the treatment of type 2 diabetes. It reduces elevated plasma glucose concentrations, mainly by suppressing hepatic glucose output. Other members of biguanides include phenformin and buformin.

Gemfibrozil and ciprofibrate belong to the fibrate family, a class of agent indicated for improving lipid levels. Other fibrates include clofibrate, fenofibrate and bezofibrate. These agents reduce hypertriglyceridaemia and hypercholesterolaemia. More importantly, their properties on elevating HDL-cholesterol and reducing small dense LDL are highly appreciated recently because circulating low HDL cholesterol and high small dense LDL are highly atherogenic in patients with type 2 diabetes. Among the fibrates, some, including fenofibrate and bezafibrate, possess some degree of glucose-lowering effect (WO 99/40904 and U.S. Pat. No. 5,304,575), while the others including clofibrate, gemfibrozil and ciprofibrate are lack of glucose-lowering effect (WO99/40904; Vuorinen-Markkola H et al. *Diabetologia* 1993, 36:161-9; Hernandez-Mijares A et al. *Nutr Metab Cardiovasc Dis* 2000, 10:1-6). As such, fibrates can be sub-divided into "glucose-lowering fibrates" and "non-glucose-lowering fibrates". A non-glucose-lowering fibrate is a fibrate that does not have statistically significant glucose lowering effect when used alone.

The combination of a hypoglycemic agent and a lipid-improving agent has already been envisaged in the art, especially for treating diabetic patients with severe hypertriglyceridaemia and hypercholesterolaemia. However, these combinations have been in the context of using respective agents to correct respective abnormalities, not anticipating additional benefits from the combinations. In fact, contradictory results were obtained depending on the drugs used in the combination. Combination of metformin and members of non-glucose-lowering fibrate, such as clofibrate has failed to show better control of hyperglycemia (WO 99/40904). On the other hand, combination of metformin and members of glucose-lowering fibrate, such as fenofibrate and bezafibrate, led to better control of hyperglycemia (WO99/40904), although this was not a synergistic effect. It was the outcome of an additive glucose-lowering effect of metformin and these fibrates, since synergism is defined as the joint action of agents so that their combined effects is greater than the algebraic sum of their individual effects (Dorland's Illustrated Medical Dictionary, 27$^{th}$ Edition). From these examples, it is obvious to a person in skill of art that better hyperglycemic control can be obtained when combining the use of metformin and a glucose-lowering fibrate, while better hyperglycemic control can not be obtained when combining the use of metformin and a non-glucose-lowering fibrate.

Surprisingly, the current inventor discovered that combined administration of metformin and gemfibrozil or ciprofibrate, two members of the non-glucose-lowering fibrates, produced an unexpected synergistic reduction of plasma glucose concentrations.

SUMMARY OF THE INVENTION

The current invention involves a pharmaceutical composition containing a combination of two active agents. The invention also involves the use of the combination composition to the preparation of a drug combination intended to treat, control and prevent type 2 diabetes or other diseases, conditions that glucose abnormality, including abnormalities in glucose level and glucose metabolism, is a component.

BRIEF DESCRIPTION OF THE TABLES

Table 1. Glucose Levels and the Metformin/Gemfibrozil Treatment.

Gemfibrozil alone did not have significant effect on glucose level ($P>0.05$).

* $P<0.05$ compared to Vehicle treated samples.

** $p<0.05$ compared to samples treated with metformin alone.

Table 2. Glucose Levels and the Metformin/Ciprofibrate Treatment.

Ciprofibrate alone did not have significant effect on glucose levels ($P>0.05$).

* P<0.05 compared to Vehicle treated samples.
** p=0.0554 compared to samples treated with metformin alone.

DETAILED DESCRIPTION OF THE INVENTION

The current invention involves a pharmaceutical composition containing a combination of a biguanide, preferably metformin and non-glucose-lowering fibrates, preferably gemfibrozil or ciprofibrate, as active agents. The invention also involves the use of a biguanide, preferably metformin and non-glucose-lowering fibrates, preferably gemfibrozil or ciprofibrate for the preparation of a drug combination intended to treat, control and prevent type 2 diabetes or other diseases, conditions that glucose abnormality, including abnormalities in glucose level and glucose metabolism, is a component.

This invention demonstrated for the first time that the selected non-glucose-lowering fibrates produced better control of hyperglycemic when combined with metformin. Furthermore, a true synergistic effect, where the effect of the combination was MORE than the sum of the respective individual agent effect, was observed with these combinations. This is very different from what the inventors of WO 99/40904 observed, where the effect of the combination of metformin and glucose-lowering fibrates (fenofibrate or bezafibrate) was actually LESS than the sum of the respective individual glucose-lowering effect. In addition, the current invention achieved a much larger magnitude of blood glucose reduction on top of the effect of metformin alone as compared to that of the combinations in invention of WO 99/40904 (−53.9 to −65.4 vs. −30 to −31 mg/dl). This synergistic glucose-lowering effect demonstrated that the combination of metformin and the selected non-glucose-lowering fibrates gemfibrozil or ciprofibrate represents a novel pharmaceutical composition.

Thus, the invention involves a pharmaceutical composition consisting of two active agents, (1) metformin in one of its pharmaceutically acceptable form, and (2) a lipid-improving agent selected from gemfibrozil and ciprofibrate in one of their pharmaceutically acceptable form, in combination with one or more pharmaceutically acceptable excipients, such as fillers, binders, dyes, flavour enhancers and the like as described in WO99/40904. Pharmaceutically acceptable form includes but not limited to all pharmaceutically acceptable salts. The composition contains a weight ratio of metformin or of its pharmaceutically acceptable form to gemfibrozil or of its pharmaceutically acceptable form ranges from 1:0.1 to 1:10. The weight ratio of metformin or of its pharmaceutically acceptable form to ciprofibrate or of its pharmaceutically acceptable form ranges from 1:0.01 to 1:10.

This composition is suitable for lowering the hyperglycemia in patients with diabetes associated with or without dyslipidemia. For those associated with dyslipidemia, the dyslipidemia is effectively controlled by this composition. This composition is also expected to be suitable for treating, controlling or preventing diseases, disorders or conditions associated with abnormal plasma glucose levels. Such abnormalities include, but not limited to diabetes mellitus, hyperglycemia, impaired glucose-tolerance, obesity, pancreatitis and other disorders where abnormal plasma glucose level is a component. Because of the presence of lipid improving agents gemfibrozil and ciprofibrate, it is further expected that the composition is suitable for treating, controlling or preventing diseases, disorders or conditions associated with abnormal plasma lipid levels such as diabetes mellitus, hyperlipidemia, hypertriglyceridemia, hypercholesterolemia and other diseases where abnormal plasma lipid level is a component. It is also expected that the complications associated with diabetes and dyslipidemia, e.g., retinopathy, neuropathy, kidney failure and cardiovascular diseases, can be treated, controlled or prevented by the composition. The composition is suitable for administering to human and non-human mammals.

The composition can be formulated for oral, inhalation, sublingual, buccal, intranasal, rectal, intravenous, subcutaneous, intramuscular, and transdermal administration, although other routes are not excluded. The composition is preferably administered orally in the form of gelatin capsules, effervescence tablets, coated or uncoated tablets, sachets, sugar-coated tablets, drinkable vials or solutions, microgranules or sustained-release or slow-release forms. Each dose unit contains 100-1000 mg of metformin and 100-1200 mg of gemfibrozil. Alternatively, each unit can have 100-1000 mg of metformin and 20-500 mg of ciprofibrate.

EXAMPLE 1

Experiment was conducted in ob/ob mice, an animal model of diabetes. Male, 8-9 week old ob/ob mice were purchased from Jackson Laboratory (Bar Harbor, Me.) and housed in a temperature and humidity controlled room with 12 hour light (6 am to 6 pm)/dark (6 pm-6 am) cycle and ad libitum of water and regular Purina chow. Animals were screened for plasma glucose levels and randomized into groups for experiments.

In this experiment, 8 animals were orally dosed with vehicle, metformin (90 mg/kg), gemfibrozil (100 mg/kg), or combination of metformin (90 mg/kg) and gemfibrozil (100 mg/kg) once a day for 3 days. Plasma glucose concentrations were determined at the end of the experiment. As showed in Table 1, metformin significantly reduced plasma glucose concentrations while gemfibrozil alone showed minimum reduction of plasma glucose and it was not statistically significant. When the two agents combined, much greater magnitude of plasma glucose reduction was observed. The glucose reducing ability of the glucose-lowering agent (metformin) was greatly enhanced by gemfibrozil. The effect of the combination (−153.2 mg/dl) was more than the sum of the respective individual agent effect (−145.3 mg/dl). This demonstrated a synergism of action with the combination.

EXAMPLE 2

Experiment was conducted in ob/ob mice. The experimental condition was the same as Working Example 1.

In this experiment, 8 animals were orally dosed with vehicle, metformin (90 mg/kg), ciprofibrate (2.5 mg/kg), or combination of metformin (90 mg/kg) and ciprofibrate (2.5 mg/kg) once a day for 4 days. Plasma glucose concentrations were determined at the end of the experiment. As showed in Table 2, metformin significantly reduced plasma glucose concentrations while ciprofibrate showed minimum effect on reducing plasma glucose and it was not statistically significant. When the two agents combined, much greater magnitude of plasma glucose reduction was observed. The glucose reducing ability of the glucose-lowering agent (metformin) was greatly enhanced by ciprofibrate. The effect of the combination (−137.8 mg/dl) was more than the sum of the respective individual agent effect (−116.3 mg/dl). This demonstrated a synergism of action with the combination.

TABLE 1

Glucose levels and the metformin/gemfibrozil treatment.

| Treatment | Day 3 (mg/dl) | Difference between Vehicle & treatment (mg/dl) |
|---|---|---|
| Vehicle | 406.8 ± 32.4 | — |
| Metformin | 318.6 ± 29.3* | −88.2 |
| Gemfibrozil | 349.7 ± 39.0 | −57.1 |
| Metformin + Gemfibrozil | 253.2 ± 20.9** | −153.2 |

TABLE 2

Glucose levels and the metformin/ciprofibrate treatment.

| Treatment | Day 4 (mg/dl) | Difference between Vehicle & treatment (mg/dl) |
|---|---|---|
| Vehicle | 383.3 ± 29.0 | — |
| Metformin | 299.2 ± 24.9* | −84.1 |
| Ciprofibrate | 351.1 ± 23.1 | −32.2 |
| Metformin + Ciprofibrate | 245.5 ± 19.4** | −137.8 |

What is claimed is:

1. A method of treating a disease, disorder or condition, said method comprising administering to a human or non-human mammal in need thereof a pharmaceutical composition consisting of (1) metformin or a pharmaceutically acceptable salt thereof, (2) a non-glucose-lowering fibrate selected from gemfibrozil or ciprofibrate, and optionally (3) one or more excipients, wherein the ratio of metformin to non-glucose-lowering fibrate is 1:0.5 to 1:2, and wherein said disease, disorder or condition is selected from the group consisting of diabetes mellitus, hyperglycemia, impaired glucose-tolerance, insulin resistant syndrome, obesity, and pancreatitis where abnormality in plasma glucose levels or glucose metabolism is a component.

2. The method according to claim 1, wherein the administration is by means of oral, inhalation, sublingual, buccal, intranasal, rectal, intravenous, subcutaneous, intramuscular, and transdermal administration.

3. The method of claim 1, wherein the glucose-lowering agent and the lipid-improving agent are mixed together to form an admixture and the admixture is administered to the human or non-human mammals.

* * * * *